US00PP35945P2

(12) United States Plant Patent
Hansen

(10) Patent No.: US PP35,945 P2
(45) Date of Patent: Jul. 2, 2024

(54) ***HOSTA* PLANT NAMED 'Affair to Remember'**

(50) Latin Name: ***Hosta* hybrid (Tratt.)**
Varietal Denomination: Affair to Remember

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 18/445,634

(22) Filed: Nov. 29, 2023

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'Affair to Remember' produces large rounded mounds of large, broadly ovate, variegated leaves with acute apices and cordate bases. The leaves are variegated having dark green margins, the centers progress from a light chartreuse to whitish green, with intermediate color separation between the margin and center of variably large segments of several shades of chartreuse. The large leaves have a slightly lustrous upper surface and glaucous underside. The campanulate flowers are near white appearing beginning in late June and continuing for almost seven weeks. Each flower is attractively subtended by a floral bract that has a dark green margin with a creamy green center and a variable blush of light purple. 'Affair to Remember' is useful in the landscape, as a container plant, a specimen, or en masse.

3 Drawing Sheets

Botanical classification: *Hosta* hybrid (Tratt.).
Variety denomination: 'Affair to Remember'.

STATEMENT REGARDING PRIOR DISCLOSURES UNDER 37 CFR 1.77(b)(6)

*Hosta* 'Affair to Remember' was first introduced by the inventor as a non-enabling description in registration of the name in early 2023 with the International Cultivar Registration Authority for the genus *Hosta*. No plants of *Hosta* 'Affair to Remember' have been sold or offered for sale in this country or anywhere in the world, nor has any enabling disclosure of the new plant been made.

BACKGROUND AND ORIGIN OF THE PLANT

The present invention relates to a new and distinct *Hosta* plant 'Affair to Remember' hereinafter also referred to as the new plant or by the cultivar name, 'Affair to Remember'. *Hosta* 'Affair to Remember' was hybridized by the inventor on Aug. 21, 2009, at a wholesale perennial nursery in Zeeland, Michigan, USA. The female parent was the proprietary unreleased hybrid known only as HOS-WGI-22B (not patented) and the male parent was 'Empress Wu' U.S. Plant Pat. No. 20,774. The seeds from this cross were harvested on Oct. 21, 2009, and planted in late fall of 2009. A single seedling selection from this cross eventually was selected as the new plant. The new plant was assigned the breeder code H9-273-1 and passed the initial evaluation in the summer of 2011. 'Affair to Remember' has been asexually propagated by division at the same nursery since 2017 and also by careful shoot tip plant tissue culture with the resultant asexually propagated plants having retained all the same traits as the original plant. *Hosta* 'Affair to Remember' has been stable and reproduced true-to-type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Angel Falls' U.S. Plant Pat. No. 28,785, 'American Sweetheart' (not patented), 'Cherry Berry' (not patented), 'Cool As a Cucumber' (not patented), 'Lakeside Love Affaire' (not patented), 'Lakeside Paisley Print' (not patented), 'Love Story' U.S. Plant Pat. No. 34,224, 'Miss America' U.S. Plant Pat. No. 32,068, 'My Fair Lady' U.S. Plant Pat. No. 35,524 'Night before Christmas' (not patented), 'Rare Breed' (not patented), and 'When I Dream' U.S. Plant Pat. No. 34,285.

The female parent is larger, more vase-shaped in habit, with larger and more cordate foliage, the white and green variegation is thinly spread in sectors throughout the leaves rather than with the lighter sector all being confined to the middle of the leaves. The male parent has a larger habit, more rounded and solid bluish-green-colored foliage, and the scapes are longer and bluish-green colored.

The habit of 'Angel Falls' is smaller and more arching in habit, deeper adaxial veins, the leaf margin is more sinuate, and the scape has fewer flowers that are more flared. 'American Sweetheart' has a larger more upright habit, more erect taller scapes, thicker and stiffer foliage, and the leaves have a lighter yellowish center early in the season. 'Cherry Berry' has a smaller habit with smaller narrower foliage, the scapes are shorter with fewer flowers of darker purple, and reddish blush in the petioles, peduncles, and young seed pods. 'Cool As a Cucumber' has a slightly smaller habit, longer more lanceolate and arching foliage, and the inner variegation color is more whitish. 'Lakeside Love Affaire' has a more whitish leaf center and the foliage and habit are both smaller. 'Lakeside Paisley Print' has a stiffer and thicker substance foliage with broader margins, narrower center variegation, and more sinuate edges, the scapes become more lavender blushed, and the flowers are darker purple. 'Love Story' has a smaller habit, the foliage is longer, more lanceolate, with more sinuate margins, and more acute apices. 'Miss America' has a larger habit, larger, stiffer, and thicker foliage, the scapes are much taller and more erect, and the flowers are larger, open wider, and have a darker lavender center stripe. 'My Fair Lady' has a smaller habit and the foliage has a more bluish-green margin and a more whitish leaf center. 'Night before Christmas' has a smaller habit, narrower and smaller foliage, the inner variegation is more white and less yellow early in the season, and there are fewer intermediate colors between the leaf margin and center. 'Rare Breed' has a smaller habit, the scapes are light green, the scape bracts are more light green without both the defined variegation and the lavender blush, and there are more flowers per scape. 'When I Dream' has foliage that is broader, more cordate, more bullate, and more sinuate, the margin color is more bluish-green, the scapes are more compact and shorter, and the flowers are lighter lavender.

Other *Hosta* cultivars may have individual traits similar to 'Affair to Remember' but the new plant differs from the above-listed cultivars and all other *Hostas* known to the applicant, by the combination of the following traits.

1. Leaves are variegated, large-sized, broadly ovate, with acute apices and cordate bases;
2. Leaf margins are dark green, the early center color is light chartreuse, and the mature center color is whitish green, with intermediate color separation between the margin and center of variably large segments of several shades of chartreuse;
3. Numerous campanulate flowers of near white on upright, creamy-green colored scapes beginning in late June for nearly seven weeks;
4. Flowers are densely arranged on scapes with the first flowers beginning to open well above the foliage;
5. Floral bracts have a variegation that subtend each flower;
6. Bract color is greenish on the margin, creamy-green in the center with a light purple blush;
7. The habit is a large-sized rounded mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source, and direction may cause the appearance of minor variations in color.

The drawings show a ten-year-old 'Affair to Remember' plant in a trial garden at a nursery in Zeeland, MI with supplement fertilizer and water as needed.

DETAILED BOTANICAL DESCRIPTION

Figure 1:
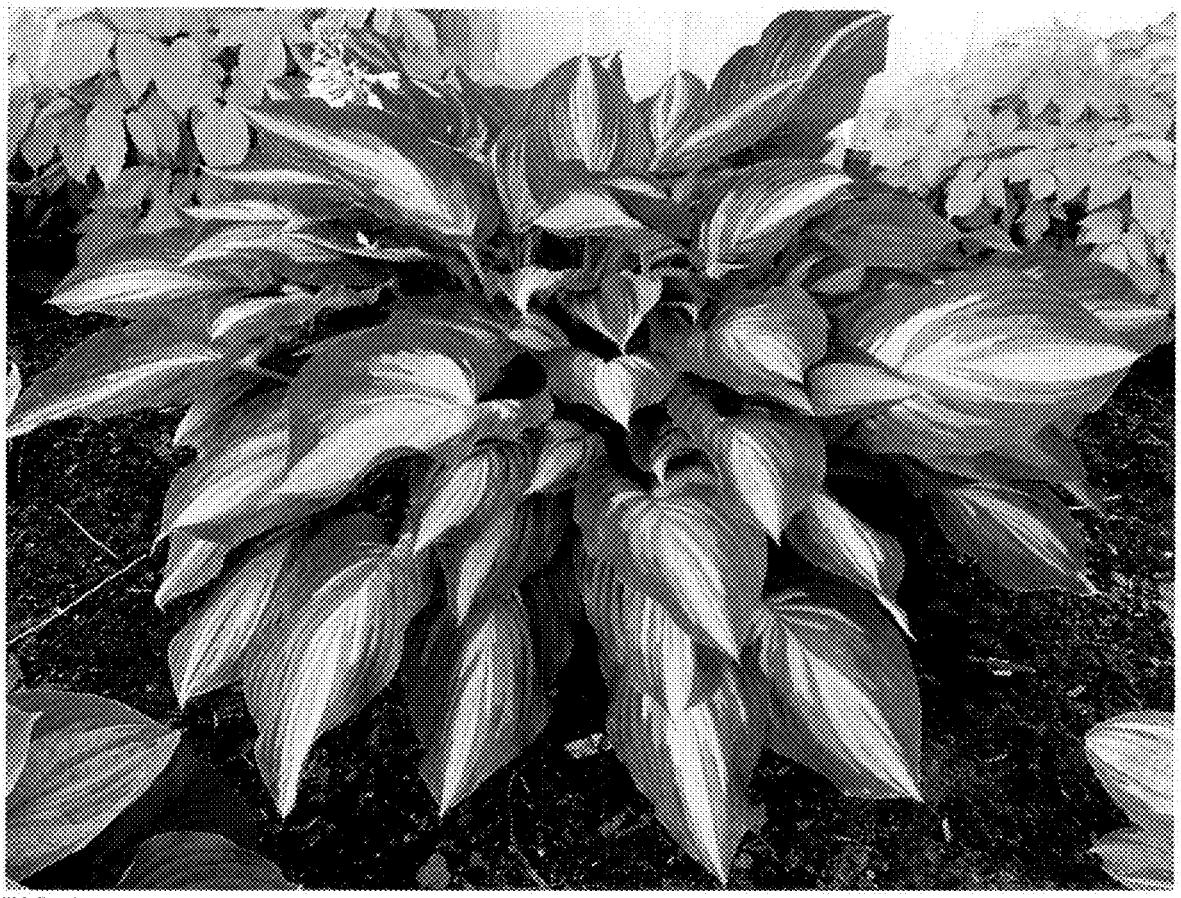
FIG. 1 shows the landscape foliage habit and color of the new plant.
Figure 2:
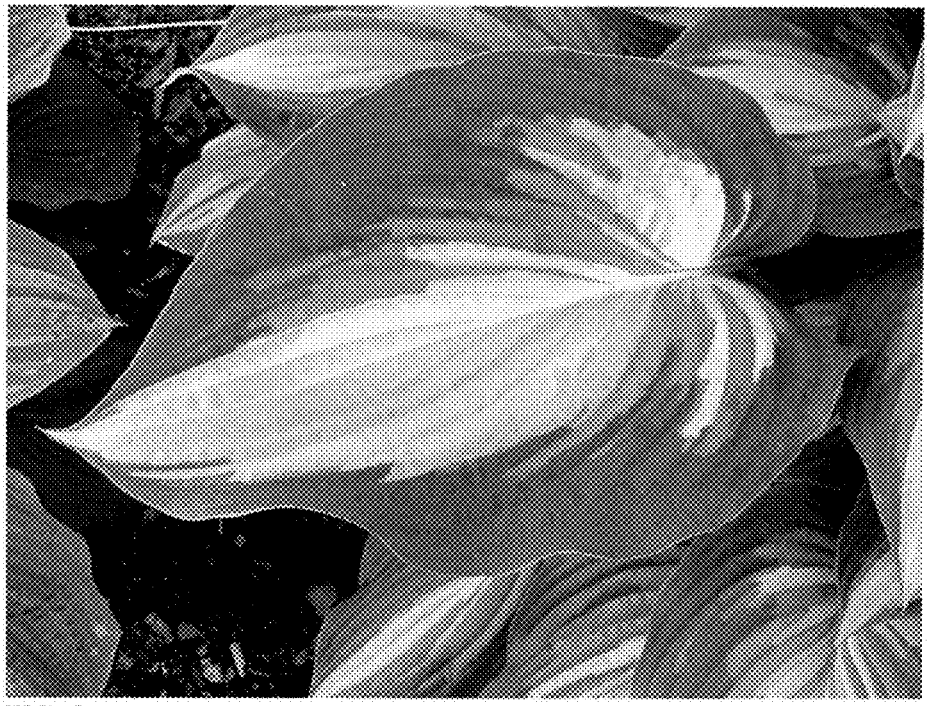
FIG. 2 shows a close-up of a leaf and variegation in the early summer.
Figure 3:
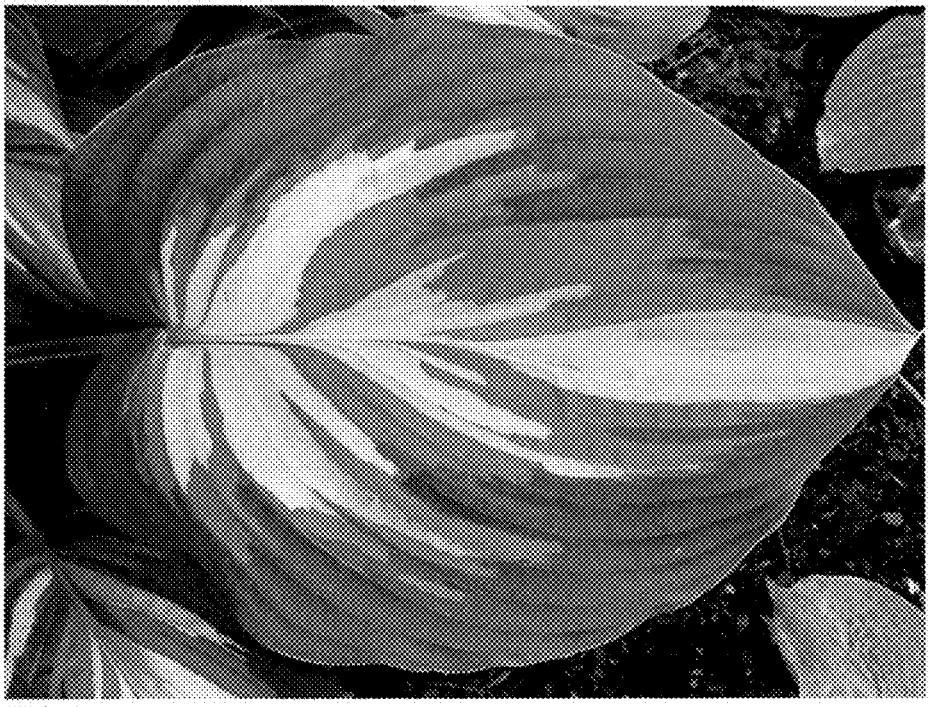
FIG. 3 shows a close-up of a leaf with variegation in the later summer.
Figure 4:
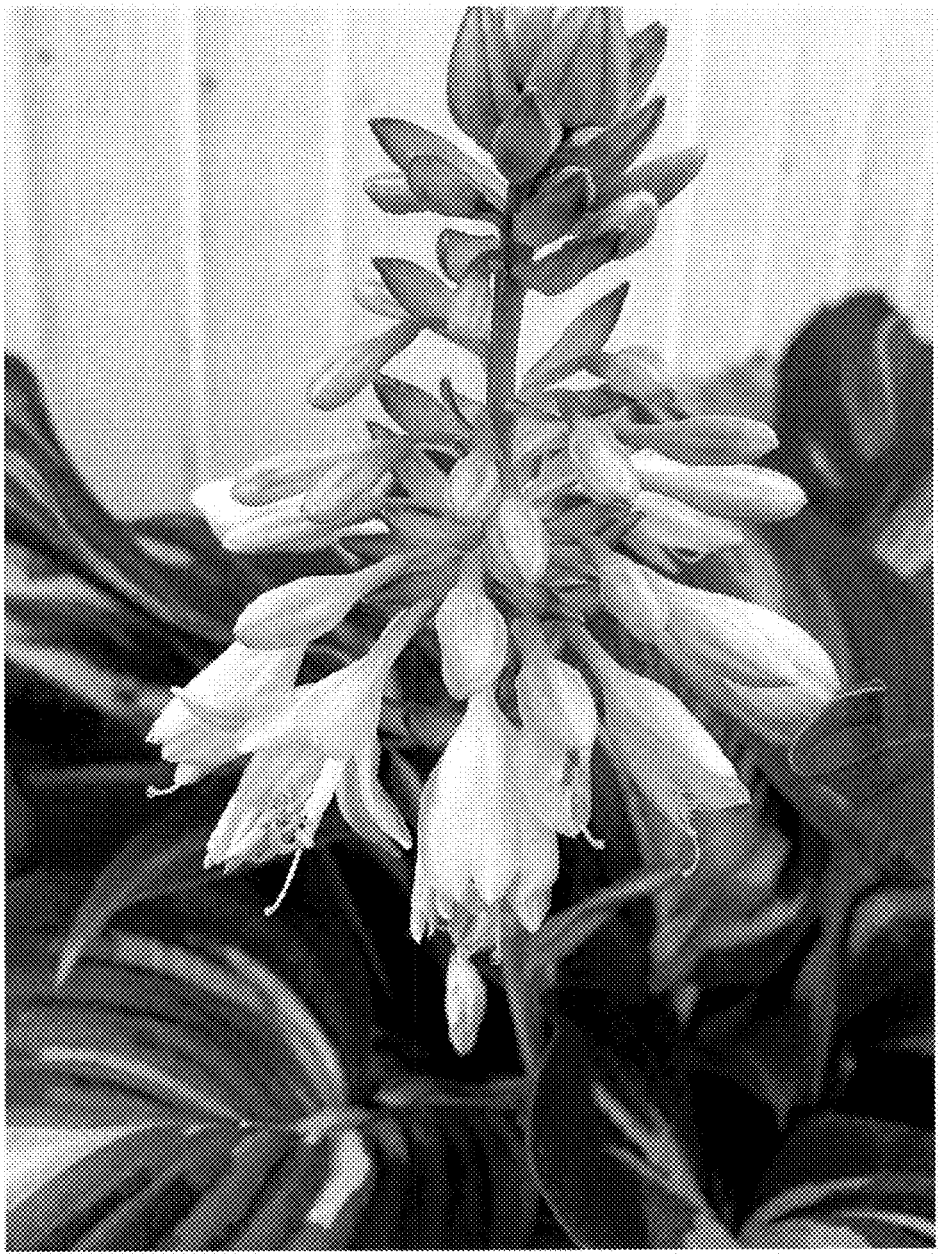
FIG. 4 shows a close-up of the scape with flowers, buds, and small variegated foliar bracts.

The following descriptions and color references are based on the 2015 edition of The Royal Horticultural Society Colour Chart except where common dictionary terms are used. The new plant, *Hosta* 'Affair to Remember', has not been observed under all possible environments. Those skilled in the art would recognize the phenotype of the new plant would differ based on maturity level or number of years without dividing. The phenotype may vary slightly with different environmental conditions, such as temperature, light, fertility, moisture, and maturity levels, but without any change in the genotype. The following observations and size descriptions are of a ten-year-old plant in a shaded trial garden in Zeeland, Michigan with supplemental water and fertilizer.

Botanical classification: *Hosta* x hybrid;

Parentage: Female or seed parent is a proprietary seedling HOS-WGI-22B; male or pollen parent is 'Empress Wu';

Propagation: Garden division and sterile shoot tip tissue culture;

Time to initiate roots from tissue culture: About three weeks;

Growth rate: Moderately vigorous;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with a basal rosette of leaves emerging from rhizomes producing a low medium-sized mound of outwardly extending petioles and leaves and arching scapes flowering above the foliage;

Plant size: Foliage height to about 74 cm above the soil to the top of the leaves, to about 105 cm tall to the top of the flowers, and to about 175 cm wide at the widest point just above the soil line;

Foliage description: Broadly ovate; acute apex; cordate base; margin entire, and slightly repand; not folded, flat, and not bullate between the veins, glabrous and smooth on both surfaces; adaxial slightly lustrous, abaxial glaucous; flexible; variegated;

Leaf blade size: To about 33 cm long and about 23 cm wide about one-third way from the base; average about 29.5 cm long and 21 cm wide;

Leaf blade color: Early season and expanding adaxial margin region nearest RHS 137B, center between RHS 1C and RHS 154D, and intermediate zone comprising nearest RHS145D, nearest RHS 146B, and nearest RHS 160D; early season and expanding abaxial margin region nearest RHS 146B, center between RHS 16D and RHS 1D, with intermediate zone comprising between RHS 139D and RHS 139C, between RHS 139D and N138D, and between RHS 145C and 138C; mid-season and mature adaxial margin nearest RHS 137B, center nearest RHS 11D, and intermediate zone comprising nearest RHS 146D, between RHS N144D and RHS 2C, between RHS 146C and RHS 146B, and between RHS 145A and RHS 146D; mid-season and mature abaxial margin between RHS 147B and RHS N138B, center nearest RHS 11D, with intermediate zone comprising colors of between RHS 191B and RHS 191C, between RHS 145B and RHS 147C, and between RHS 146D and RHS 145A;

Veins: 13 to 14 pairs with midrib; slightly impressed adaxial and costate and smooth abaxial;

Vein color: Young adaxial veins toward margin nearest RHS 146D, center between RHS 146D and RHS N144A; young abaxial veins toward margin nearest RHS 146D, center region nearest RHS 145C, and intermediate zone between RHS 139D and RHS 139C, between RHS 139D and RHS N138D, and between RHS 145C and RHS 138C; mature adaxial veins toward margin nearest RHS 145C, and center nearest RHS 157B, mature abaxial margin nearest RHS 138B and center nearest RHS 158D;

Petiole: Glabrous and matte both adaxial and abaxial; moderately concavo-convex; stiff; to 42 cm long and 22 mm wide at the base and about 10 mm deep, average about 37 cm long and 16 mm wide and 8 mm deep;

Petiole color: Adaxial margin between RHS 137A and RHS 137B, center nearest RHS 4D; abaxial margin nearest RHS 137B, center nearest RHS 155B;

Flower description:

Buds one to two days prior to opening: Clavate with acute apex and narrow tube and rounded base; about 42 mm long and 12 mm in diameter at the widest portion in the bulb, tube to about 15 mm long and to about 3 mm diameter at the base, gradually tapering from bulb;

Bud color: Nearest RHS 85C;

Flowers: Perfect; incomplete; campanulate; attitude outwardly to slightly downwardly; to 55 mm long to exserted pistil; corolla to 44 mm long and 44 mm wide at apex, fused in basal 20 mm, free in the distal 24 mm, decreasing in size distally; corolla tube portion 16 mm long and gradually tapering to 3 mm diameter at base; with rounded base; flowers tightly arranged on scape;

Flowering lasting: Persists for a normal period, usually about one day on plant;

Flowering period: Scapes remain effective with flowers beginning late June for nearly seven weeks; with about 64 flowers per scape; mostly secund;

Fragrance: No detectable fragrance;

Tepals: Two sets of three; clavate; entire margins; acute apex; fused in basal 20 mm; glabrous adaxial and abaxial; inner set with 1 mm to 2 mm wide translucent margin; outer set to about 13 mm wide and 44 mm long; inner set to about 12 mm wide and 44 mm long;

Tepal color: Both sets identical; adaxial nearest RHS 76D in the 3 mm longitudinal center and nearest RHS NN155D along edges, abaxial lighter than RHS 76D;

Gynoecium: Single; to about 55 mm long; superior;

*Style*.—Cylindrical; glabrous; to about 50 mm long and 0.5 mm diameter; mostly straight with distal 2 mm slightly arcuate upwards; color distally nearest RHS NN155C transitioning to nearest RHS 155C in the proximally.

*Stigma*.—Puberulent; tri-lobed; about 1 mm long and 1.5 mm diameter; color nearest RHS NN155B.

*Ovary*.—Ellipsoidal; superior; apex rounded; base rounded to truncate; sides slightly furrowed, about 4 mm long and 2.5 mm diameter; color nearest RHS 145A.

Androecium: Six;

*Filaments*.—Six; cylindrical; approximately 47 mm long and 0.5 mm in diameter; curved or bent upwardly about 90° in the distal 6 mm; color distally nearest RHS NN155C transitioning to nearest RHS 155C in the proximally.

*Anthers*.—Oblong with rounded ends; basifixed, longitudinally dehiscent; about 5.0 mm long and 2.0 mm wide when fully developed; color between RHS 159A and RHS 159C.

*Pollen*.—Abundant; spherical; less than 0.1 mm long; color nearest RHS 11C.

Peduncle: Cylindrical; usually one per mature division; about 8 per plant; glabrous; moderately glaucous; erect; to about 105 cm tall, and about 8 mm in diameter at the base, average about 88.5 cm tall and 7 mm diameter at base;

Inflorescence: Flowering portion about 43 cm long and 7 cm wide; with variegated bracts subtending each flower;

Peduncle color: Proximal portion below leaves between RHS 160D and RHS 158C and the distal portion between RHS 155A and RHS 147D;

Pedicel: Cylindrical; glabrous; slightly lustrous; to about 10 mm long and 2 mm diameter, decreasing distally; attitude outwardly to slightly arcuate outwardly;

Pedicel color: Between RHS 160D and RHS 158C;

Floral bracts: Each flower normally subtended by a single variegated bract; lanceolate; narrowly acute apex and truncate base; entire margin; glabrous and slightly glaucous abaxial and adaxial; to about 100 mm long 28 mm wide, decreasing distally; variegated margin about 2 to 3 mm wide;

Bract color: At flowering adaxial and abaxial margin between RHS 138A and RHS 147B, adaxial center nearest RHS 158D with faint to moderate blush of nearest RHS N74D, abaxial center nearest RHS 158D with a faint blush of nearest RHS N74D;

Fruit and seeds: Not yet observed;

Disease and pest resistance: Resistance to pests (including: *Odocoileus virginianus* and *Oryctotagus cuniculus*) and diseases common to *Hostas* is equal that typical of other cultivars;

Growth: The plant grows best and shows best coloration with plenty of moisture, adequate drainage, and light shade, but is able to tolerate some drought when mature.

Hardiness: At least from USDA zone 3 through 8.

It is claimed:

1. A new and distinct *Hosta* plant named 'Affair to Remember' as herein described and illustrated.

* * * * *